(12) United States Patent
Ge et al.

(10) Patent No.: US 10,071,552 B2
(45) Date of Patent: Sep. 11, 2018

(54) SENSING A PROPERTY OF A FLUID

(71) Applicant: HEWLETT-PACKARD DEVELOPMENT COMPANY, L.P., Houston, TX (US)

(72) Inventors: Ning Ge, Palo Alto, CA (US); Zhiyong Li, Singapore (SG); Leong Yap Chia, Singapore (SG); Wai Mun Wong, Singapore (SG)

(73) Assignee: HEWLETT-PACKARD DEVELOPMENT COMPANY, L.P., Houston, TX (US)

( * ) Notice: Subject to any disclaimer, the term of this patent is extended or adjusted under 35 U.S.C. 154(b) by 0 days.

(21) Appl. No.: 15/547,133

(22) PCT Filed: Apr. 30, 2015

(86) PCT No.: PCT/US2015/028570
§ 371 (c)(1),
(2) Date: Jul. 28, 2017

(87) PCT Pub. No.: WO2016/175840
PCT Pub. Date: Nov. 3, 2016

(65) Prior Publication Data
US 2018/0009224 A1 Jan. 11, 2018

(51) Int. Cl.
*B41J 2/14* (2006.01)
*G01N 27/414* (2006.01)

(52) U.S. Cl.
CPC ........ *B41J 2/14153* (2013.01); *G01N 27/414* (2013.01)

(58) Field of Classification Search
CPC ............... B41J 2/04508; B41J 2/04506; B41J 2/04503; B41J 2/04505; B41J 2/0451; B41J 2/04513; B41J 2/04515; B41J 2/04518; B41J 2/0452; B41J 2/04521;
(Continued)

(56) References Cited

U.S. PATENT DOCUMENTS

| | | |
|---|---|---|
| 4,589,970 A | 5/1986 | Ligtenberg et al. |
| 7,988,265 B2 | 8/2011 | Smith |
| 8,878,257 B2 | 11/2014 | Parris et al. |

(Continued)

OTHER PUBLICATIONS

Molina, J., et al., Integration of ISFET/MIM Structures Using a Conventional Sub-micron CMOS-based Processing Technology for pH Detection Applications with High-sensitivity. Retrieved from the internet. http://elsevier.conference-services.net/resources/247/2514/pdf/BITE2011_0079.pdf> [retrieved on Mar. 13, 2015], 1 page.

*Primary Examiner* — Kristal Feggins
(74) *Attorney, Agent, or Firm* — HP Inc. Patent Department

(57) ABSTRACT

In an example, a device for sensing a property of a fluid may include an ion-sensitive field effect transistor (ISFET) having a gate, a source, and a drain. The device may also include a first metal element in contact with the gate and a switching layer in contact with the first metal layer. A resistance state of the switching layer is to be modified through application of an electrical field of at least a predefined strength through the switching layer and is to be retained in the switching layer following removal of the electrical field. The device may also include a metal plate in contact with the switching layer, in which the metal plate is to directly contact the fluid for which the property is to be sensed.

20 Claims, 5 Drawing Sheets

(58) Field of Classification Search
CPC ............... B41J 2/04525; B41J 2/04526; B41J 2/04535; B41J 2/04536
See application file for complete search history.

(56) References Cited

U.S. PATENT DOCUMENTS

| | | |
|---|---|---|
| 2005/0230271 A1 | 10/2005 | Levon et al. |
| 2011/0031986 A1 | 2/2011 | Bhat et al. |
| 2013/0158378 A1 | 6/2013 | Berger et al. |
| 2013/0280813 A1 | 10/2013 | Rothberg et al. |
| 2014/0209983 A1 | 7/2014 | Burgi et al. |

SENSING A PROPERTY OF A FLUID

BACKGROUND

Inkjet devices are widely used for precisely and rapidly dispensing small quantities of fluid. Inkjet devices eject droplets of fluid out of a nozzle by creating a short pulse of high pressure within a firing chamber. This ejection process is typically repeated thousands of times per second during a printing operation. Inkjet devices are typically implemented using semiconductor devices, such as thermal inkjet (TIJ) devices or piezoelectric inkjet (PIJ) devices. For example, a TIJ device includes a heating element (e.g., resistor) in the firing chamber along with other integrated circuitry. To eject a droplet, an electrical current is passed through the heating element, which generates heat that vaporizes a small portion of the fluid within the firing chamber. A vapor bubble is formed, which forces a small droplet out of the firing chamber through the nozzle. The electrical current is then turned off and the heating element cools, which causes the vapor bubble to collapse and more fluid to be drawn into the firing chamber.

BRIEF DESCRIPTION OF THE DRAWINGS

Features of the present disclosure are illustrated by way of example and not limited in the following figure(s), in which like numerals indicate like elements, in which.

DETAILED DESCRIPTION

Figure 1:
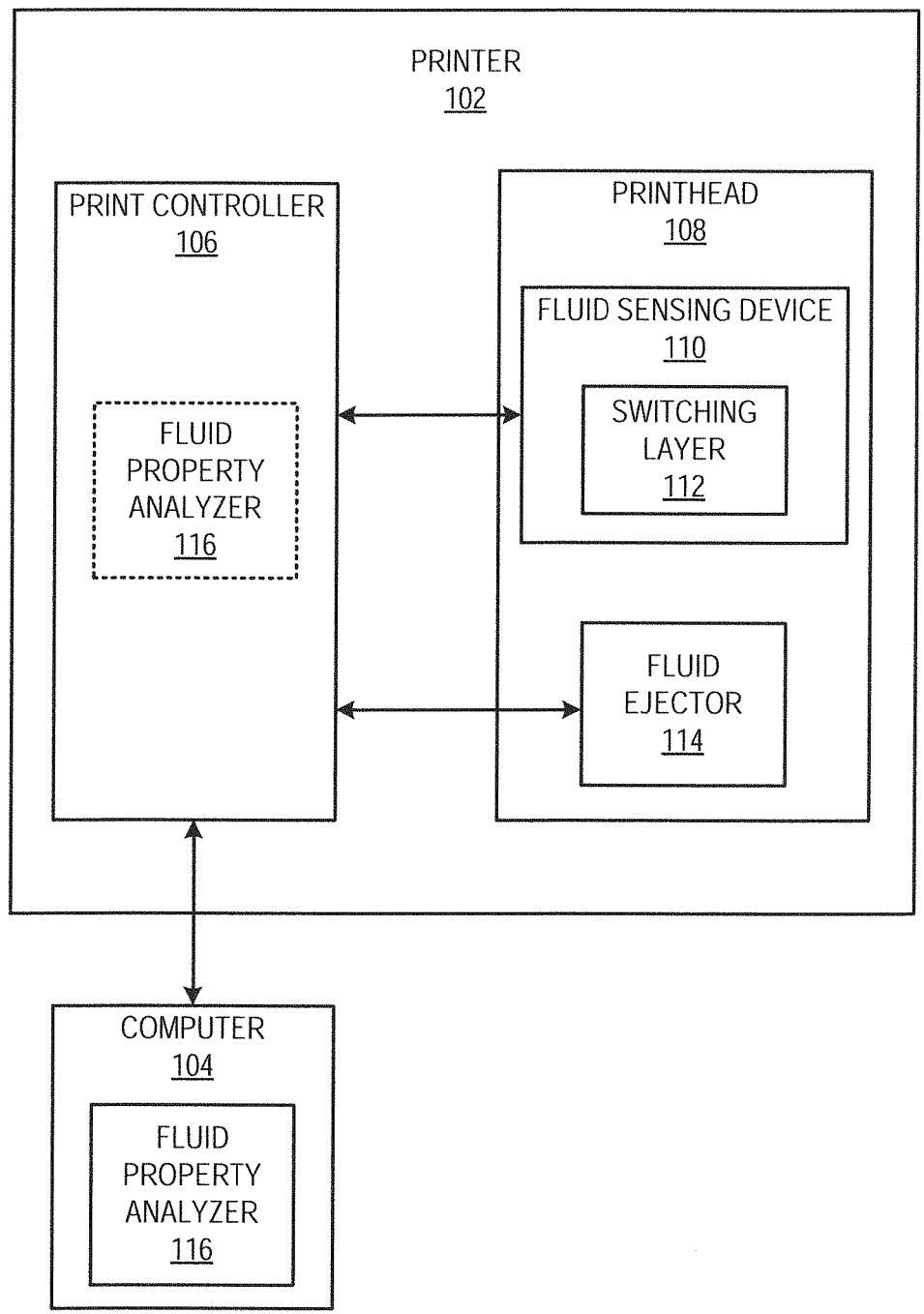
FIG. 1 shows a simplified block diagram of a printing system, according to an example of the present disclosure.

For simplicity and illustrative purposes, the present disclosure is described by referring mainly to an example thereof. In the following description, numerous specific details are set forth in order to provide a thorough understanding of the present disclosure. It will be readily apparent however, that the present disclosure may be practiced without limitation to these specific details. In other instances, some methods and structures have not been described in detail so as not to unnecessarily obscure the present disclosure. As used herein, the terms "a" and "an" are intended to denote at least one of a particular element, the term "includes" means includes but not limited to, the term "including" means including but not limited to, and the term "based on" means based at least in part on.

Disclosed herein is a fluid sensing device, a printhead including the fluid sensing device, and a method for operating the fluid sensing device. The fluid sensing device disclosed herein may be provided in a printhead to sense a property of a fluid contained in a fluid chamber of the printhead. In one example, the fluid sensing device may be implemented to differentiate between different fluid properties, such as pigment and non-pigment inks. In another example, the fluid sensing device may be implemented to determine the health of a fluid, such as whether an ink has surpassed its expiration, which may lead to pigment settling and kogation issues. As a further example, the fluid sensing device may be implemented to determine whether the fluid is from a deviant or counterfeit supplier. As a yet further example, the fluid sensing device may be implemented to determine whether an ink was properly mixed.

As discussed in greater detail herein below, the fluid sensing device may include an ion-sensitive field-effect transistor (ISFET). The sensing principle of an ISFET is based on the gathering of a charge causing a transistor threshold voltage shift at an ion-solid interface at a sensing layer. Depending on the ion concentration, e.g., as indicated by pH level for hydrogen ions in a fluid, the accumulated charge will cause a transistor threshold voltage Vt shift through changes in the surface charge change. The transistor threshold voltage Vt shift may be measured electrically through monitoring of the resistance of the transistor between a drain and a source (Rds). That is, the resistance of the transistor (Rds) may describe the relationship between the pH level and the threshold voltage Vt. The ISFET may include a sensor that is to be submerged in the fluid, in which the charging distribution for the ISFET will change and eventually vary the threshold voltage of the transistor. Therefore, property, such as the pH level, of the fluid may be detected through the resistor change by monitoring a change in the drain to source current.

The fluid sensing device may also include a switching layer positioned between a metal plate and the ISFET, in which the metal plate may operate as a sensor for the ISFET. The switching layer may be set to have one of a first resistance state and a second resistance state, in which the first resistance state has a lower resistance level than the second resistance state. When in the first resistance state, the switching layer may short a capacitor in the fluid sensing device, which may prevent the ISFET from performing a sensing operation. However, when in the second resistance state, the switching layer may enable a high performance capacitor to be formed in the fluid sensing device, which may enable the ISFET to perform a sensing operation on a fluid. In other words, the fluid sensing device may be non-operational when the switching layer is in the first resistance state and may be operational when the switching layer is in the second resistance state. In addition, the resistance state of the switching layer may be reversible, and may therefore enable the fluid sensing device to selectively detect or not detect a property of a fluid. In one regard, the switching layer may be formed of a memristive material.

Through implementation of the fluid sensing device disclosed herein, components of the fluid sensing device may be formed to have a relatively smaller size as compared to conventional fluid sensing devices that do not employ a metal plate that is in direct contact with a fluid to be tested and a switching layer. The metal plate may have dimensions that are approximately 15 µm×15 µm, whereas conventional fluid sensing devices may include sensor caps that are 50 µm×50 µm in size. Additionally, the switching layer in the fluid sensing device disclosed herein may be formed to have a relatively small thickness, for instance, approximately 5-15 nm, and may be formed of a material having a high dielectric constant (k), e.g., a high-K dielectric material. As such, the sensitivity of the fluid sensing device may be relatively higher than conventional fluid sensing devices. In this regard, therefore, the fluid sensing device disclosed herein may be relatively smaller than conventional fluid sensing devices while still improving performance.

With reference first to FIG. 1, there is shown a simplified block diagram of an example printing system 100. It should be understood that the printing system 100 depicted in FIG. 1 may include additional components and that some of the components described herein may be removed and/or modified without departing from a scope of the printing system 100. For instance, the printing system 100 may include any reasonable number of printers, the printers may include any reasonable number of printheads, and the printheads may include any reasonable number of nozzles.

As shown in FIG. 1, the printing system 100 may include a printer 102, which may be coupled to a computer 104. The printer 102 is depicted as including a print controller 106 and a printhead 108. The printhead 108 is depicted as including a fluid sensing device 110 and a fluid ejector 114. The fluid sensing device 110 is further depicted as including a switching layer 112. Although not shown, the printhead 108 may be in fluidic communication with a fluid supply, which may be separate from or integrated with the printhead 108, and may supply fluid, such as ink, dye, precursor, etc., to the printhead. As discussed in greater detail herein below with respect to FIG. 2, the fluid received from the fluid supply may be ejected from a nozzle in the printhead 108.

Generally speaking, the print controller 106 is to control operations of the printhead 108, for instance to control a fluid ejector 114 to cause a fluid to be expelled through a nozzle and applied onto a print medium. The print controller 106 may also control other components (not shown) of the printer 102, such as, a print medium feeding mechanism, a carriage actuator, etc. The print controller 106 may be a central processing unit (CPU), a microprocessor, a microcontroller, an application specific integrated circuit (ASIC), a processor core, or the like.

According to an example, the print controller 106 is to also control operations of the fluid sensing device 110 to detect a property of the fluid contained in a chamber of the printhead 108. The fluid sensing device 110 may detect a property of the fluid through electrochemical detection of ion concentration in the fluid. For example, the fluid sensing device 110 may measure the pH of the fluid, where pH is a measure of the activity of solvated hydrogen ions. The pH range of a fluid such as ink in a printhead may vary as the fluid ages and is used over time. For example, the pH range for some inks may range from 8.5 down to 5.5, where pH 7.0 is neutral. The change in pH versus percentage change in weight loss may vary for different inks depending on the particular ion combination for the ink solution.

In operation, the print controller 106 may drive the fluid sensing device 110 to measure fluid ion concentration. The print controller 106 may obtain samples of electrical output from the fluid sensing device 110 representative of fluid ion concentration. In an example, the print controller 106 provides the samples to the computer 104. As shown, the computer 104 may include a fluid property analyzer 116 implemented using machine-readable instructions, hardware, or a combination thereof. The fluid property analyzer 116 may analyze the electrical samples and derive fluid properties from the analysis. In some examples, the functionality of the fluid property analyzer 116 may be implemented in the print controller 106 rather than the computer 104, as indicated by the dashed box of the fluid property analyzer 116 in the print controller 106.

In addition, the print controller 106 may control whether or not the fluid sensing device 110 is to detect the property of the fluid contained in the printhead chamber. In other words, and as described in greater detail herein below, the print controller 106 may control whether the fluid sensing device 110 is "turned on" (operational) or "turned off" (non-operational) by controlling the resistance state of the switching layer 112 in the fluid sensing device 110. In one regard, the ability to turn off the detection of the fluid property may reduce the total amount of data being collected by the print controller 106, which may enable the print controller 106 to operate more efficiently. In another regard, this ability may enable the print controller 106 to activate selected ones of a plurality of fluid sensing devices to enable focalized sensing.

Figure 2:
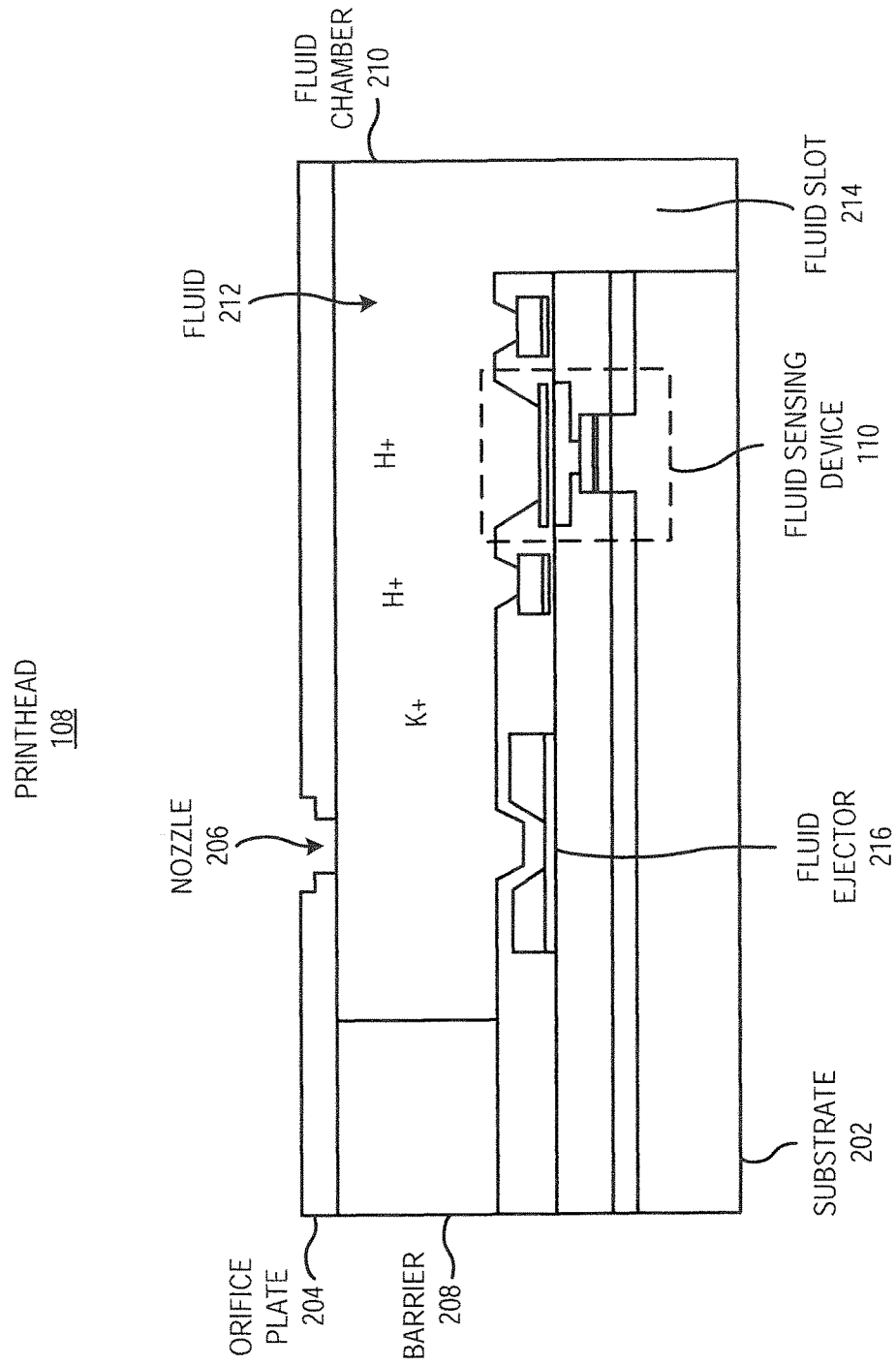
FIG. 2 shows a simplified cross-sectional view of a portion of a printhead, according to an example of the present disclosure.

Turning now to FIG. 2, there is shown a simplified cross-sectional view of a portion of an example printhead 108. It should be understood that the printhead 108 depicted in FIG. 2 may include additional components and that some of the components described herein may be removed and/or modified without departing from a scope of the printhead 108.

The printhead 108 is depicted as including a substrate 202 and an orifice plate 204 spaced from the substrate 202. A nozzle 206 is depicted as being formed in the orifice plate 204. In addition, a barrier 208 and a fluid chamber 210 are depicted as being positioned between the substrate 202 and the orifice plate 204. The fluid chamber 210 is to store a fluid 212, such as ink, dye, precursor material, finishing material, etc., and the fluid 212 may be supplied into the fluid chamber 210 through a fluid slot 214, which may be connected to a fluid supply (not shown). In addition, the barrier 208 may be a polymeric material (e.g., IJ500® (available from 3M® Corporation), SU8), and the fluid chamber 210 may be formed in the barrier 208. The orifice plate 204 may be metal or a polymeric material (e.g., Kapton® (form DuPont®), SU8). As shown, the fluid chamber 210 is in fluidic communication with the nozzle 206.

The printhead 108 is further depicted as including a fluid ejector 216 and the fluid sensing device 110, which may both be disposed on the substrate 202. The fluid ejector 216 may be a thermal actuator, a piezoelectric actuator, or the like, and may be positioned in the fluid chamber 210 in line or approximately in line with the nozzle 206. The fluid sensing device 110 may detect a property of the fluid through electrochemical detection of ion concentration in the fluid as described in greater detail herein below with respect to FIG. 3. Although not explicitly described, the printhead 108 may include circuitry for controlling the fluid ejector 216 and the fluid sensing device 110.

Figure 3:
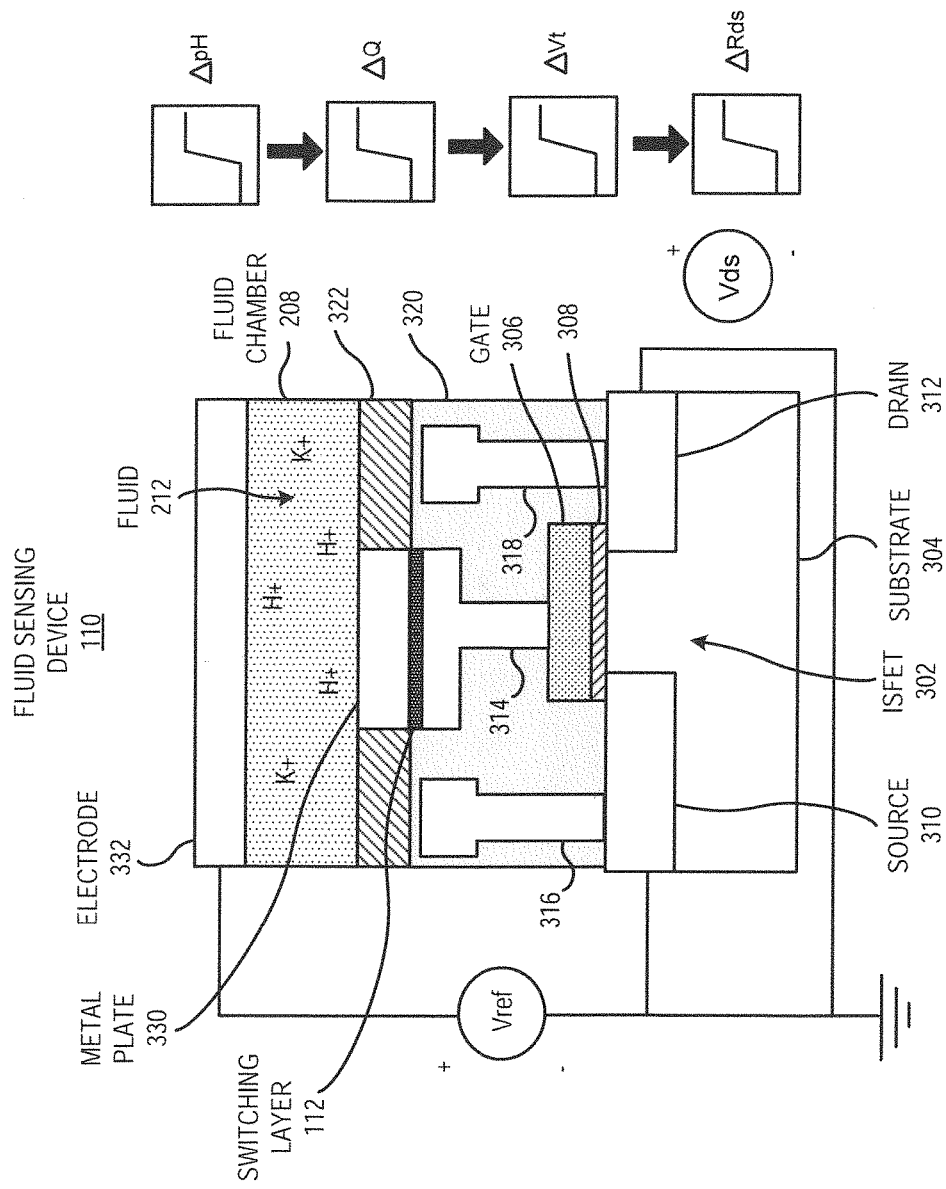
FIG. 3 shows a cross-sectional view of a portion of a fluid sensing device, according to an example of the present disclosure.

With reference now to FIG. 3, there is shown a cross-sectional view of a portion of an example fluid sensing device 110. It should be understood that the fluid sensing device 110 depicted in FIG. 3 may include additional components and that some of the components described herein may be removed and/or modified without departing from a scope of the fluid sensing device 110.

The fluid sensing device 110 is depicted as including an ion-sensitive field effect transistor (ISFET) 302 formed in a substrate 304. The substrate 304 may correspond to a portion of the substrate 202 of the printhead 108 and may be formed of silicon. Alternatively, the substrate 304 may be a different substrate. The ISFET 302 is depicted as including a gate 306 formed on a gate oxide layer 308. The gate 306 may be formed of a polysilicon material. The ISFET 302 is also depicted as including a source 310 and a drain 312, which are in contact with the gate oxide layer 308, and may form respective diffusion regions. In an example, field oxide is not used to isolate transistors. Rather, polysilicon is patterned and used as a mask to selectively diffuse regions in the substrate 302. Hence, a transistor may include a polysilicon ring separating one diffusion region from another. It is to be understood that such a structure is one example and that other examples may include substrates having traditional field oxide separating diffusion regions.

In an example, the fluid sensing device 110 is implemented using N-type metal-oxide semiconductor (NMOS) logic such that the substrate 302 includes a P-type substrate and the diffusion regions corresponding to the source 310 and the drain 312 include N+ doped regions. NMOS logic may be used for implementing the fluid sensing device 110. However, it is to be understood that the fluid sensing device 110 may be implemented using P-type metal-oxide semiconductor (PMOS) logic or complementary metal oxide semiconductor (CMOS) logic. In the case of PMOS logic, the substrate 302 may include N-type silicon and the diffusion regions corresponding to the source 310 and the drain 312 may include P+ doped regions. The configuration for N-wells in N-well CMOS logic are similar to the PMOS configuration, and the configuration for P-wells in P-well CMOS logic are similar to the NMOS configuration.

The gate oxide layer 308 may include a dielectric oxide material, such as silicon dioxide (SiO2), a high-k dielectric material, such as hafnium oxide (HfO2) or aluminum oxide (Al2O3), or the like. A polysilicon layer may be formed and patterned over the gate oxide layer 308 resulting in formation of a polysilicon gate 306 between the source 310 and the drain 312. A metal layer may be formed and patterned over the polysilicon gate 306 resulting in the formation of a first metal element 314, a second metal element 316, and a third metal element 318 that are respectively in electrical contact with the polysilicon gate 306, source 310, and the drain 312.

A dielectric material 320 may be positioned to generally isolate the first metal element 314, the second metal element 316, the third metal element 318, and the polysilicon gate 306 from each other with the exception of the specific electrical contacts described above. The dielectric material 320 may be formed of, for example, silicon dioxide. A passivation layer 322 may be formed on the dielectric material 320, such that the passivation layer 322 is separated from the first metal element 314, the second metal element 316, and the third metal element 318 by a section of the dielectric material 320. The passivation layer 322 may also be formed of a dielectric material, such as silicon nitride (Si3N4), silicon carbide (SiC), a combination thereof, or the like.

As also shown in FIG. 3, a switching layer 112 may be provided in electrical contact with the first metal element 314. The switching layer 112 is also depicted as being in electrical contact with a metal plate 330, such that the switching layer 112 is sandwiched between the first metal element 314 and the metal plate 330. The metal plate 330 is further depicted as extending through the passivation layer 322 and being exposed to the fluid 212 contained in the fluid chamber 208. According to a particular example, the metal plate 330 is formed of TaAl.

The switching layer 112 may be formed of a switching oxide, such as a metallic oxide, may have a relatively small thickness, and may be formed of a high-K material. By way of example, the switching layer 112 may have a thickness in the range of between about 1 nm to about 50 nm and may have a dielectric constant (K) of at least about 6 to 80. Specific examples of suitable switching oxide materials may include silicon nitride, titanium dioxide, magnesium oxide, titanium oxide, zirconium oxide, hafnium oxide, vanadium oxide, niobium oxide, tantalum oxide, chromium oxide, molybdenum oxide, tungsten oxide, manganese oxide, iron oxide, cobalt oxide, copper oxide, zinc oxide, aluminum oxide, gallium oxide, silicon oxide, germanium oxide, tin dioxide, bismuth oxide, nickel oxide, yttrium oxide, gadolinium oxide, and rhenium oxide, among other oxides. In addition to the binary oxides presented above, the switching oxides may be ternary and complex oxides such as silicon oxynitride. The oxides presented may be formed using any of a number of different processes such as sputtering from an oxide target, reactive sputtering from a metal target, atomic layer deposition (ALD), oxidizing a deposited metal or alloy layer, etc. According to an example, the switching layer 112 may formed directly on the surface of the first metal element 314 and/or the surface of the metal plate 330.

The resistance level of the switching layer 112 may be changed in response to various programming conditions and the switching layer 112 is able to exhibit a memory of past electrical conditions. For instance, the switching layer 112 may be programmed to have a first resistance state or a second resistance state and may retain the programmed resistance state following removal of a programming condition. Particularly, the resistance level of the switching layer 112 may be changed through application of a voltage or current, in which the voltage or current may cause mobile dopants in the switching layer 112 to move, which may alter the electrical operation of the switching layer 112. That is, for instance, the resistance levels of the switching layer 112 may correspond to different electrical fields applied to the switching layer 112 through application of different voltages or currents. By way of example, the switching layer 112 may be programmed to have a lower resistance level through application of a higher voltage or current.

After removal of the voltage or current, the locations and characteristics of the dopants in the switching layer 112 are to remain stable until the application of another programming or writing electrical field. That is, the switching layer 112 remains at the programmed resistance level following removal of the voltage or current. In addition, the resistance level of the switching layer 112 may be changed after the resistance level has been set or programmed, i.e., the resistance state is reversible. For instance, following the setting of the switching layer 112 to have a first resistance state, another voltage or current, for instance, having a reverse polarity, may be applied to the switching layer 112, which may cause the mobile dopants to move in an opposite direction, thereby causing the switching layer 112 to have a second resistance state. In this example, the second resistance state may correspond to a higher resistance level as compared with the first resistance state. When in the first resistance state, a voltage or current may flow between the metal plate 330 and the first metal element 314 through the switching layer 112. When in the second resistance state, the switching layer 112 may prevent the flow of a voltage or reading current between the metal plate 330 and the first metal element 314. In this regard, when in the first resistance state, the switching layer 112 may prevent a capacitor from being formed by the first metal element 314 and the metal plate 330. In other words, the switching layer 112, when in the first resistance state, may prevent the ISFET from being operational and may thus prevent the ISFET from performing a sensing operation. In contrast, when in the second resistance state, the switching layer 112 may enable the formation of a relatively high capacitance capacitor between the first metal element 314 and the metal plate 330. In other words, the switching layer 112, when in the second resistance state, may enable the ISFET to be operational.

As discussed above, the print controller 106 may control operations of the fluid sensing device 110. In one example, the print controller 106 may control whether the fluid sensing device 110 is to detect the property of the fluid 212 by changing the resistance state of the switching layer 112. That is, the print controller 106 may set the switching layer 112 to be in the first resistance state, i.e., have a first resistance level, in which the switching layer 112 is to short a capacitor in the fluid sensing device 110 and thus render the fluid sensing device 110 non-operational.

In the first resistance state, the switching layer 112 may thus prevent the fluid sensing device 110 from detecting the property of the fluid 212. In this example, the print controller 106 may cause a first electrical field having a sufficiently high strength to be created across the switching layer 112, which may cause the switching layer 112 to switch from the first resistance state to the second resistance state, in which the resistance level of the switching layer 112 is higher than the resistance level under the first resistance state. As the resistance level of the switching layer 112 is increased, the capacitance between the metal plate 330 and the first metal element 314 may be increased, thereby enabling the fluid sensing device 110 to detect the property of the fluid 212.

As further shown in FIG. 3, an electrode 332 may be positioned in an aligned and spaced relation to the metal plate 330 such that fluid 212 in the fluid chamber 208 may be present between the metal plate 330 and the electrode 332. The electrode 332 may be formed on the orifice plate 204 (FIG. 2) over the ISFET 302. In addition, the electrode 332 may be capacitively coupled to the ISFET 302 through fluid 212 in the fluid chamber 208, the metal plate 330, the switching layer 112, and the first metal element 314. In some examples, the fluid sensing device 110 may be disposed in a fluid chamber 208 that does not contain a fluid ejector 216.

In an example, the orifice plate 204 is formed of metal and the electrode 332 is formed as a protrusion of the orifice plate 204. In such case, the orifice plate 204 and the electrode 332 may include nickel (Ni) with a palladium (Pa) or Titanium (Ti) coating, for example. In another example, the orifice plate 204 may be formed of a polymer material and the electrode 332 may be embedded in the polymer material. In such case, the electrode 332 may be formed of TaAl, for example.

The polysilicon gate 306 together with the respective portions of the first metal layer 314, the switching layer 112, and the metal plate 330 in electrical contact with the polysilicon gate 306 may form a "floating-gate" of metal-oxide field effect transistor (MOSFET) having the source 310 and the drain 312 (assuming N-MOS). Together with the dielectric layer 320, the MOSFET is the ISFET. The metal elements 314, 316, 318 and the metal plate 330 may be formed of any suitable metal or metal alloy, for instance, Aluminum (Al), Aluminum copper (AlCu), Tantalum aluminum (TaAl), etc. The electrode 332 may also be formed of any of these types of metal or metal alloy materials.

In operation, the source 310 may be coupled to a reference voltage (e.g., electrical ground) and a voltage may be applied to the electrode 332. The electrode 332 may thus essentially act as the reference gate of the ISFET. The voltage between the electrode 332 and the source 310 is the gate-to-source voltage, referred to as Vgs. The charge distribution for the ISFET will change according to the ion concentration in the fluid 212. As the charge distribution changes, the threshold voltage of the ISFET changes. For example, if the fluid sensing device 110 is to measure pH, then the ISFET's threshold voltage depends on the pH of the fluid 212 in contact with the metal plate 330. A change in the threshold voltage of the ISFET may be measured by measuring the change in drain-to-source current (Ids) for a particular drain-to-source voltage (Vds). In general, materials for the electrode 332 and the metal plate 330 may be selected such that the threshold voltage of the ISFET changes over time in response to changes in a particular ion combination (pH described herein by way of example). Changes in the threshold voltage may be detected through measurements of drain-to-source current given a particular drain-to-source voltage.

The operations described above may be performed when the resistance state of the switching layer 112 is set to cause a capacitor to be operational in the fluid sensing device 110. However, if the resistance state of the switching layer 112 is set to allow the flow of a current or a voltage from the metal plate 330 to the first element 314, a change in drain-to-source current (Ids) may not be measured and thus the fluid sensing device 110 may be in the "off" condition.

The print controller 106 may control the resistance state of the switching layer 112 through application of a changing voltage or a changing current, or a changing voltage or a changing current having a reverse polarity, through the switching layer 112 as applied between the electrode 332 and the source 310. In this example, the switching layer 112 may be formed such that the voltage or current level required to change the resistance state of the switching layer 112 (e.g., a changing voltage or a changing current) is higher than the voltage or current level used by the fluid sensing device 110 to detect a property of the fluid 212 (e.g., a reading voltage or a reading current). That is, the voltage applied to the electrode 332 during a sensing operation of the fluid 212 may not generate a sufficiently strong electrical field through the switching layer 112 to cause the resistance state of the switching layer 112 to be changed.

Figure 4:
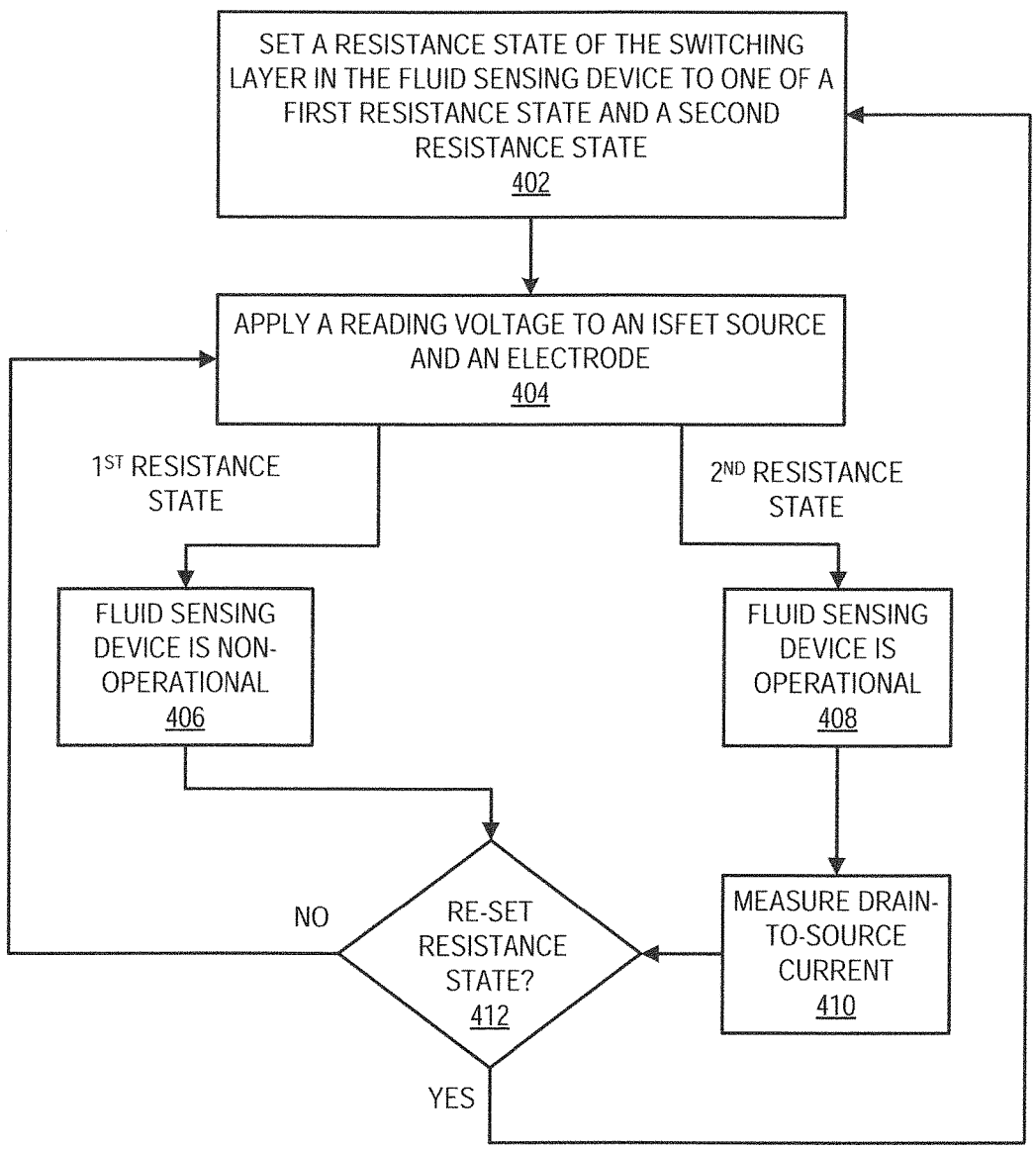
FIG. 4 shows a flow diagram of a method of operating a fluid sensing device, according to an example of the present disclosure.

With reference now to FIG. 4, there is shown a flow diagram of an example method 400 of operating a fluid sensing device 110. It should be understood that the method 400 depicted in FIG. 4 may include additional operations and that some of the operations described herein may be removed and/or modified without departing from the scope of the method 400. The description of the method 400 is made with reference to the features depicted in FIG. 1-3 for purposes of illustration and thus, it should be understood that the method 400 may be implemented in fluid sensing devices having features different from those shown in those figures.

At block 402, a resistance state of the switching layer 112 in the fluid sensing device 110 may be set to one of a first resistance state and a second resistance state. For instance, if the switching layer 112 is in the first resistance state, the switching layer 112 may be set to the second resistance state. Likewise, if the switching layer 112 is in the second resistance state, the switching layer 112 may be set to the first resistance state. As discussed above, the first resistance state may correspond to a lower resistance level than the second resistance state. In addition, the switching layer 112 may be set to the first resistance state from the second resistance state through application of a changing voltage or changing current through the switching layer 112. Likewise, the switching layer 112 may be set to the second resistance state from the first resistance state through application of an opposite polarity changing voltage or changing current through the switching layer 112.

As also discussed above, the switching layer 112 may be positioned between the metal plate 330 and the first metal element 314 that is coupled to the gate 306 of an ion-sensitive field effect transistor (ISFET) 302. In addition, the metal plate is positioned in a spaced relation to an electrode 332 that is capacitively coupled to the gate 306 of the ISFET 302.

According to an example, at block 402, the print controller 106 may determine that the resistance state of the switching layer 112 is to be set or changed and may cause a voltage source (not shown) to apply a changing voltage across the switching layer 112. As discussed above, the changing voltage may be higher than the voltage used to determine a property of the fluid 212 (e.g., reading voltage) and may be applied through the electrode 332 and the source 310 as shown in FIG. 3.

At block 404, a reading voltage may be applied to the source 310 of the ISFET 302 and the electrode 332. Particularly, the printer controller 106 may cause or control a voltage source to apply a reading voltage between the electrode 332 and the source 310 as shown in FIG. 3. The reading voltage may be sufficiently lower than the writing voltage to prevent unintentionally changing the resistance state of the switching layer 112. In this regard, the reading voltage may be selected to be a voltage level that is sufficient to detect a property of the fluid 212 without causing the resistance state of the switching layer 112 to change. Thus, although the reading voltage may cause some change in the resistance level of the switching layer 112, the change may be insufficient to cause the resistance state of the switching layer 112 to change. In any regard, when the switching layer 112 is set to the first resistance state, a voltage or a current may readily flow through the capacitor formed by the first metal element 314 and the metal plate 330, which may short the fluid sensing device 110 and may thus render the fluid sensing device 110 non-operational, as indicated at block 406. In this instance, a drain-to-source current in the ISFET 302 may not exist and thus, the ISFET 302 may effectively be turned off.

At block 408, however, when the switching layer 112 is set to the second resistance state, the capacitor formed by the first metal element 314, the switching layer 112, and the metal plate 330 may have a high capacitance, which may render the fluid sensing device 110 operational. In addition, at block 410, a drain-to-source current of the ISFET 302 may be measured following block 408. In addition, the measured drain-to-source current of the ISFET 302 may be communicated to the print controller 106. Alternatively, the print controller 106 may receive the detected currents and may determine the measured drain-to-source current of the ISFET 302. The print controller 106 may implement a fluid property analyzer 116 to analyze the measured drain-to-source current and determine a property of the fluid 212. Alternatively, the print controller 106 may forward the measured drain-to-source current to a computer 104, which may implement a fluid property analyzer 116 to determine a property of the fluid 212. In any regard, the fluid property analyzer 116 may obtain multiple drain-to-source measurements over time and may derive ion concentration measurements of the fluid 212 from changes in the drain-to-source measurements over time.

Following either of blocks 406 and 410, a determination may be made as to whether the resistance state of the switching layer 112 is to be re-set or changed. For instance, the print controller 106 may determine that a fluid sensing device 110 that is currently off is to be turned on, i.e., to sense a property of the fluid 212. Alternatively, the print controller 106 may determine that a fluid sensing device 110 that is currently on is to be turned off, i.e., to stop sensing a property of the fluid 212 or that the fluid sensing device 110 is to remain in its current operating condition.

In response to a determination that the resistance state of the fluid sensing device 110 is not to be re-set or changed, the method 400 may end. Alternatively, the print controller 106 may cause a voltage to be applied again at block 404 and blocks 406-412 may be repeated. However, in response to a determination that the resistance state of the fluid sensing device 110 is to be re-set or changed, the printer controller 106 may cause the resistance state of the switching layer 112 to be re-set or changed at block 402. In addition, blocks 404-412 may be repeated.

Some or all of the operations set forth in the method 400 may be contained as utilities, programs, or subprograms, in any desired computer accessible medium. In addition, the method 400 may be embodied by a computer program, which may exist in a variety of forms both active and inactive. For example, they may exist as machine readable instructions, including source code, object code, executable code or other formats. Any of the above may be embodied on a non-transitory computer-readable storage medium.

Examples of non-transitory computer-readable storage media include computer system RAM, ROM, EPROM, EEPROM, and magnetic or optical disks or tapes. It is therefore to be understood that any electronic device capable of executing the above-described functions may perform those functions enumerated above.

Figure 5:
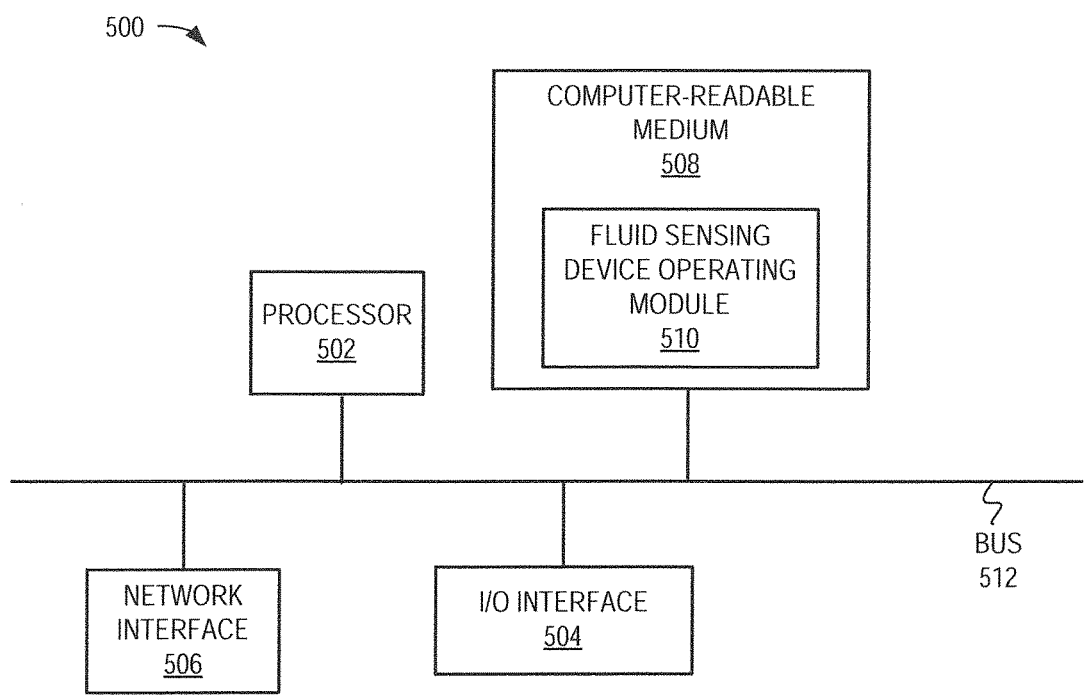
FIG. 5 shows a schematic representation of a computing device, which may include components of the printer depicted in FIG. 1, according to an example of the present disclosure.

Turning now to FIG. 5, there is shown a schematic representation of a computing device 500, which may include components of the printer 102 depicted in FIG. 1, according to an example. The computing device 500 may include a processor 502, such as the print controller 106, and an input/output interface 504. The input/output interface 504 may provide an interface with an input device, such as a touchscreen interface, etc., and an output device, such as a display. The computing device 500 may also include a network interface 506, such as a Local Area Network LAN, a wireless 802.11x LAN, a 3G mobile WAN or a WiMax WAN, through which the computing device 800 may connect to a network (not shown). The computing device 500 may further include a computer-readable medium 508 on which is stored sets of machine-readable instructions. Each of these components may be operatively coupled to a bus 512, which may be an EISA, a PCI, a USB, a FireWire, a NuBus, a PDS, or the like.

The computer-readable medium 508 may be any suitable medium that participates in providing instructions to the processor 502 for execution. For example, the computer-readable medium 508 may be non-volatile media, such as an optical or a magnetic disk; volatile media, such as memory. As shown, the computer-readable medium 508 may store a fluid sensing device operating module 510, which the processor 502 may implement to operate the fluid sensing device 110 depicted in FIG. 3. The fluid sensing device operating module 510 may thus be a set of machine readable instructions pertaining to the method 400.

Although described specifically throughout the entirety of the instant disclosure, representative examples of the present disclosure have utility over a wide range of applications, and the above discussion is not intended and should not be construed to be limiting, but is offered as an illustrative discussion of aspects of the disclosure.

What has been described and illustrated herein are examples of the disclosure along with some variations. The terms, descriptions and figures used herein are set forth by way of illustration only and are not meant as limitations. Many variations are possible within the scope of the disclosure, which is intended to be defined by the following claims—and their equivalents—in which all terms are meant in their broadest reasonable sense unless otherwise indicated.

What is claimed is:

1. A device for sensing a property of a fluid, the device comprising:
   an ion-sensitive field effect transistor (ISFET) having a gate, a source, and a drain;
   a first metal element in contact with the gate;
   a switching layer in contact with the first metal element, wherein a resistance state of the switching layer is to be modified through application of an electrical field of at least a predefined strength through the switching layer, and wherein the switching layer is to retain the resistance state following removal of the electrical field; and
   a metal plate in contact with the switching layer, wherein the metal plate is to directly contact the fluid for which the property is to be sensed.

2. The device according to claim 1, wherein the switching layer is formed of a switching material that has a first resistance state in which the switching layer has a first resistance level, and a second resistance state in which the switching layer has a second resistance level, wherein the first resistance level is lower than the second resistance level, and wherein in the first resistance state, the switching layer prevents a selected voltage from being established in the ISFET.

3. The device according to claim 2, wherein the switching layer is switchable between the first resistance state and the second resistance state through application of electrical fields having different properties through the switching layer, and wherein the switching layer is formed of a high-K material.

4. The device according to claim 1, further comprising:
   a second metal element in contact with the source; and
   a third metal element in contact with the drain.

5. The device according to claim 4, further comprising:
   a dielectric layer, wherein the first metal element, the second metal element, the third metal element, and the gate are positioned within the dielectric layer; and
   a passivation layer positioned in contact with the dielectric layer, wherein the passivation layer is to directly contact the fluid, and wherein the metal plate extends through the passivation layer.

6. The device according to claim 1, wherein the gate comprises a polysilicon material and is formed on a gate oxide layer.

7. The device according to claim 1, further comprising:
   an electrode disposed in a spaced relationship with the metal plate such that the fluid is to be positioned between the electrode and the metal plate, and wherein the electrode is capacitively coupled to the gate of the ISFET.

8. The device of claim 1, further comprising:
   a dielectric layer, wherein the first metal element and the gate are positioned within the dielectric layer.

9. The device of claim 8, further comprising:
   a passivation layer over the dielectric layer, wherein the metal plate extends through the passivation layer.

10. The device of claim 9, further comprising an electrode spaced apart from the metal plate and the passivation layer by a space in which the fluid is to be provided, the electrode to receive a programming voltage to change the resistance of the switching layer.

11. The device of claim 10, wherein the electrode to receive a reading voltage to sense the property of the fluid.

12. The device of claim 11, wherein a current between the drain and the source of the ISFET responsive to the reading voltage represents the property of the fluid.

13. A printhead comprising:
    an orifice plate;
    a nozzle formed in the orifice plate;
    a fluid ejector;
    a fluid chamber formed between the fluid ejector and the orifice plate;
    a fluid property sensing device disposed to detect a property of fluid contained in the fluid chamber, wherein the fluid property sensing device includes:
      an ion-sensitive field effect transistor (ISFET) having a gate, a source, and a drain;
      a metal plate exposed to the fluid chamber;
      a switching layer in contact with the metal plate, wherein a resistance state of the switching layer is to be modified through application of an electrical field through the switching layer, and wherein the switching layer is to retain the resistance state following removal of the electrical field; and
      an electrode positioned in spaced, aligned relation to the metal plate, wherein the electrode is capacitively coupled to the gate of the ISFET.

14. The printhead according to claim 13, wherein the switching layer is formed of a switching material that has a first resistance state in which the switching layer has a first resistance level, and a second resistance state in which the switching layer has a second resistance level, wherein the first resistance level is lower than the second resistance level, and wherein in the first resistance state, the switching layer prevents the ISFET from sensing the fluid property.

15. The printhead according to claim 14, wherein the switching layer is switchable between the first resistance state and the second resistance state through application of electrical fields having different properties from each other through the switching layer.

16. The printhead according to claim 13, wherein the fluid property sensing device further includes:
    a first metal element in contact with the gate;
    a second metal element in contact with the source;
    a third metal element in contact with the drain; and
    wherein the gate comprises a polysilicon material and is formed on a gate oxide layer.

17. A method of operating a fluid sensing device, the method comprising:
    setting a resistance state of a switching layer in the fluid sensing device to one of a first resistance state and a second resistance state, wherein the switching layer is positioned between a metal plate and a first metal element that is coupled to a gate of an ion-sensitive field effect transistor (ISFET), wherein the metal plate is positioned in an aligned and spaced relation to an electrode that is capacitively coupled to the gate of the ISFET; and
    applying a reading voltage to a source of the ISFET and the electrode, wherein the fluid sensing device is non-operational when the switching layer is set to the first resistance state, and the fluid sensing device is operational when the switching layer is set to the second resistance state.

18. The method according to claim 17, further comprising:
    measuring a drain-to-source current of the ISFET with the selected voltage established between the source and the drain of the ISFET.

19. The method according to claim 17, wherein the resistance state of the switching layer is set to the first resistance state, the method further comprising:
  setting the resistance state of the switching layer from the first resistance state to the second resistance state through application of an electrical field across the switching layer.

20. The method according to claim 17, wherein the metal plate and the electrode are to be positioned in direct contact with a fluid that is to be sensed.

* * * * *

UNITED STATES PATENT AND TRADEMARK OFFICE
CERTIFICATE OF CORRECTION

PATENT NO. : 10,071,552 B2  
APPLICATION NO. : 15/547133  
DATED : September 11, 2018  
INVENTOR(S) : Ning Ge et al.

Page 1 of 1

It is certified that error appears in the above-identified patent and that said Letters Patent is hereby corrected as shown below:

On the Title Page

On page 2, Column 1, item (56), below "Burgi et al." insert -- foreign patent documents, WO2003073088 09/2003 TOUMAZOU et al. -- as a new entry.

Signed and Sealed this  
Thirteenth Day of August, 2019

Andrei Iancu  
*Director of the United States Patent and Trademark Office*